(12) United States Patent
Russo et al.

(10) Patent No.: US 9,181,201 B2
(45) Date of Patent: *Nov. 10, 2015

(54) METHOD OF TREATMENT OF ANXIETY DISORDER COMORBID WITH DEPRESSION DISORDER

(71) Applicants: ACHÉ LABORATÓRIOS FARMACÊUTICOS S.A., Guarulhos (BR); ACHÉ INTERNATIONAL (BVI) LTD., Tortola (VG)

(72) Inventors: Valter Freire Torres Russo, Itapira (BR); Elisa Mannochio De Souza Russo, Itapira (BR)

(73) Assignees: ACHE LABORATORIOS FARMACEUTICOS S.A., Sao Paulo (BR); ACHE INTERNATIONAL (BVI) LTD., Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 14/251,985

(22) Filed: Apr. 14, 2014

(65) Prior Publication Data

US 2015/0018365 A1   Jan. 15, 2015

Related U.S. Application Data

(63) Continuation-in-part of application No. 13/824,063, filed as application No. PCT/BR2011/000374 on Sep. 22, 2011, now Pat. No. 8,735,578.

(30) Foreign Application Priority Data

Sep. 24, 2010   (BR) .................................. 1003506

(51) Int. Cl.
  *A61K 31/497*   (2006.01)
  *C07D 239/88*   (2006.01)

(52) U.S. Cl.
  CPC .................................. *C07D 239/88* (2013.01)

(58) Field of Classification Search
  None
  See application file for complete search history.

(56) References Cited

U.S. PATENT DOCUMENTS 4,841,051 A * 6/1989 Shiozawa ............. C07D 471/04
544/279

* cited by examiner

*Primary Examiner* — Dennis Heyer
*Assistant Examiner* — Daniel M Podgorski
(74) *Attorney, Agent, or Firm* — B. Aaron Schulman, Esq.; Stites & Harbison, PLLC.

(57) ABSTRACT

The present invention relates to a method for treating comorbid anxiety disorders and depression disorders, as well as for preventing depression disorders in individuals affected by anxiety disorders, by administering a therapeutically effective amount of the compound of general formula (I):

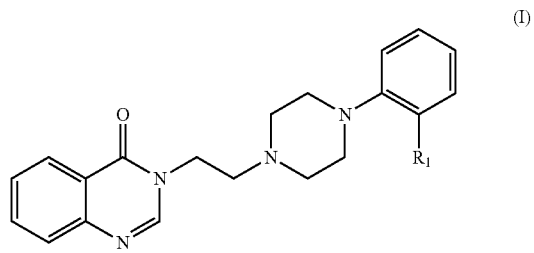

wherein $R_1$ is —$OCH_3$ or —CN
or suitable pharmaceutical salts, hydrates or anhydrates thereof.

4 Claims, 3 Drawing Sheets

METHOD OF TREATMENT OF ANXIETY DISORDER COMORBID WITH DEPRESSION DISORDER

FIELD OF THE INVENTION

The present invention relates to a method for treating comorbid anxiety disorders and depression disorders, as well as for preventing depression disorders in individuals affected by anxiety disorders, by administering a therapeutically effective amount of the compound of general formula (I):

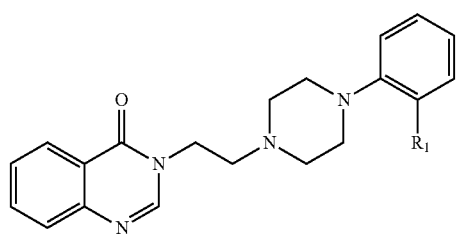

wherein $R_1$ is —$OCH_3$ or —CN
or suitable pharmaceutical salts, hydrates or anhydrates thereof.

BACKGROUND OF THE INVENTION

According to the World Health Organization (WHO) it is estimated that mental and neurological diseases affect nearly 700 million people in the world, which represents one third of all cases of non-communicable diseases.

Anxiety disorders are defined by psychic conditions comprising symptoms common to an acute or excessive anxiety setting, which plays a key role in the behavioral and psychological processes of the individual, resulting in losses on his professional and social performance.

According to the Anxiety and Depression Association of America—ADAA, anxiety disorders are the most common mental illnesses in the United States, affecting about 40 million adults above 18 years, i.e. 18% of the population.

In Brazil, the most recent statistical study regarding the prevalence of mental illness is *São Paulo Megacity Mental Health Survey*, a study conducted in great Sao Paulo sponsored by FAPESP. This study, whose statistics were published in the Oxford Textbook of Community Mental Health (2011 ed., page 55), the incidence of anxiety disorders affects 19.9% of a population, out of 29.6% of individuals who alleged to have been affected by mental disorders within 12 months before the interview.

It is estimated that only one third of individuals affected by any anxiety disorder receive treatment. This low index is caused by factors such as prejudice, fear, incomprehension, lack of information about this mental disturbance and inability to seek assistance due to the condition itself.

According to DSM-IV—Diagnostic and Statistical Manual of Mental Disorders—Fourth Edition, Text Revision) anxiety disorders include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to general medical conditions, substance-induced anxiety disorder and anxiety disorder without specific cause.

Although this manual intends to categorize the various anxiety disorders through descriptive and observable definitions, in practice, these definitions represent only a part of the clinic observed reality. Frequently, health care professionals face health frameworks whose standardization to the disorders described in DSM is inadequate for patients under treatment. This is due to phenomena such as comorbidity and frequent setting of atypical and sub-clinical symptoms.

A collaborative study of the World Health Organization about the psychological problems in general health treatment ("*The World Health Organization (WHO) Collaborative Study on Psychological Problems in General Health Care*") pointed out that anxiety and depression disorders are the most frequent co-occurring psychiatric disorders. In this study, among patients diagnosed with anxiety disorder, 45% also had depression disorder, of which 40% also had anxiety disorder.

According to DSM-IV, depression disorders include major depressive disorder or major depression, dysthymic disorder or dysthymia and minor depression. This category also includes atypical mood disorders, whose development occur under special or singular circumstances, which are psychotic depression, postpartum depression, seasonal affective disorder and bipolar disorder.

Two long-term studies indicated the existence of a correlation between anxiety and depression. The study, known as "*Munich follow-up Study*" (Wittchen H U, Essau C A. *Comorbidity of anxiety disorders and depression: does it affect course and outcome? Psychiatry Psychobiol.* 1989, 4: 315-323; *Lifetime and Six-month Prevalence of Mental Disorders in the Munich Follow-up Study—Eur. Arch. Psychiatry Clin. Neurosci.* 1992, 241: 247-258) demonstrated that most individuals with both disorders initially presented pure anxiety diagnosis before depression. This same observation was made in the study known as "*Zurich Cohort Study of Young Adults*" (Angst J, M Vollrath, Merikangas K R, Ernst c. *Comorbidity of anxiety and depression in the Zurich cohort study of young adults*. In: Maser J D, Cloninger C R, eds. *Comorbidity of Mood and Anxiety Disorders*. Washington, D.C.: American Psychiatric Press, 1990: 123-137). These studies also evidenced that individuals originally diagnosed with pure depression tend to remain with this diagnosis. These observations demonstrated that anxiety has a strong correlation with depression, and could trigger it over time.

In general terms, individuals from comorbid anxiety disorders to depression disorders have more severe symptoms, which leads to a more accentuated disability percentage than it is observed in patients with any of these pure disorders. The course of the disease is less favorable in patients with comorbid condition, since the response to antidepressant treatment and remission of symptoms is significantly lower (*Medicographia*. 2009, 31: 126-131).

Although anxiety disorders are different from depression disorders, people with depression usually develop symptoms similar to anxiety disorders, such as nervousness, irritability, sleeping problems and concentration. Even so, each disorder has its own cause, as well as behavioral and emotional symptoms. Many of the individuals who develop depression showed some history of anxiety disorder in their lives. Although there is no evidence that a disorder causes the other, it is clearly evident that many individuals are affected by both (source: http://www.adaa.org/understanding-anxiety/depression).

In a recent research on the determining factors for the lack of response in patients with treatment-resistant depression, the presence of any comorbid anxiety disorder was the most significant factor associated with this lack of response (Souery D, Oswald P, Massat I, et al; *Group for the Study of Resistant Depression. Clinical factors associated with treatment resistance in major depressive disorder: results from a European multicenter study. J. Clin. Psychiatry.* 2007, 68: 1062-1070).

Much progress was made on the understanding that the comorbid anxiety disorders to depression disorders are a very common condition. If not treated properly, patients with this comorbidity have a recovery lower than patients with another pure condition, besides of presenting more severe symptoms and in higher number than those observed in patients diagnosed with depression.

Presently, there are several classes of medicines that are used in the treatment of anxiety disorders.

Benzodiazepines for long corresponded to the group of medicines of choice for the treatment of anxiety disorders. Although they are effective in relieving symptoms related to these disorders, this class of medicines triggers tolerance, causes physical dependence and, when the use is interrupted after a long period of time, causes withdrawal syndrome. Due to these disadvantages, this type of medicine is usually prescribed for short periods of time, especially for patients with a history of alcohol abuse or of development of medicine dependence. Examples of medicines belonging to this class are alprazolam, clonazepam, diazepam, lorazepam and oxazepam, among others.

Buspirone is a partial agonist of $5\text{-HT}_{1A}$ receptors which has effect in the treatment of anxiety. Since it acts on the serotonergic system, this medicine is associated with a lower incidence of side effects when compared to benzodiazepines. The time required to establish the anxiolytic effect provided by this medicine is considerably long, from four to six weeks to be effective, which is a disadvantage and restricts its use in cases of emergency. Besides this factor, many clinical professionals do not believe that its effectiveness is comparable to that of benzodiazepines (Uriel Halbreich and Stuart A. Montgomery—*Pharmacotherapy for Mood, Anxiety, and Cognitive Disorders*—American Psychiatric Press. Ed. 2000, pg. 336).

Many medicines originally developed for treating depression relieved the symptoms observed in anxiety disorders.

Tricyclic antidepressants such as imipramine, desipramime, amitriptyline and clomipramine, among others, were the first medicines developed to treat depression that demonstrated a relieve of symptoms observed in anxiety disorders. The medicines have In common structures comprised by three fused rings, and most of them act as serotonin and norepinephrine reuptake inhibitors, blocking the serotonin transporter and the norepinephrine transporter. They also act on muscarinic receptors of cholinergic system and act as antagonists on histamine receptors $H_1$ and $H_2$. Due to the multiple activity on several receptors and transporters, tricyclic drugs are associated with a wide range of side effects, the most dangerous being those related to cardiac and central nervous systems, in case of overdose. Besides this factor, these medicines also trigger the withdrawal syndrome, requiring a gradual reduction of dose until the complete withdrawal. The withdrawal syndrome caused by this class of medicines includes symptoms such as nausea, vomiting, diaphoresis, unrest, insomnia, headaches, dizziness, runny nose, tremor, chills, weakness, fatigue, musculoskeletal pain, abdominal spasms, malaise, anxiety and irritability, among others (*Can. Med. Assoc. J.* 1981, 125(5): 420-422).

With the development of modern medicines for the treatment of depression, which target a narrower range of receptors or carriers, these new medicines, considered more selective, occupied the place of the tricyclic antidepressants and also earned their place in the treatment of anxiety disorders.

Among the preferred medicines currently employed the selective serotonin reuptake inhibitors, known as ISRS (or SSRI in English) are worthy to mention. Examples of compounds belonging to this class are paroxetine, fluoxetine, citalopram, escitalopram and sertraline. As buspirone, the therapeutic effect of ISRSs takes between four to six weeks to be reached achieved, which is a disadvantage. These medicines have a smaller range of side effects, the most common of them being weight gain, insomnia and particularly sexual dysfunction. It is estimated that the percentage of patients that develop some kind of sexual dysfunction associated with the use of ISRSs is between 30% to 60% of patients treated (Gregorian R S et al., *Ann. Pharmacother.*, 2002, 36 (10): 1577-1589), an extremely high percentage and that certainly interferes significantly with treatment compliance. Moreover, as in previous cases, the ISRSs also trigger the withdrawal syndrome whose main symptoms are nausea, headaches, electric shock sensations, insomnia, tremor, confusion, nightmares and vertigo, as well as psychological symptoms such as anxiety, unrest, crying, irritability and aggressiveness.

Another class of medicines that have been currently highlighted for treating anxiety is comprised by the serotonin-norepinephrine reuptake inhibitors, known as IRSN (or SNRI in English). This class of medicines includes compounds such as venlafaxine and duloxetine. As dual inhibitors, these medicines act on serotonin norepinephrine reuptake inhibition, being subject to the same side effects and withdrawal syndrome observed for ISRSs. Therapeutically, these medicines act by inhibiting serotonin reuptake when used in low concentration and, when used in high concentrations, they inhibit norepinephrine reuptake.

Agomelatine is an antidepressant that was recently placed on the market. This medication has a mixed action mechanism, acting through the agonism of melatoninergic $MT_1$ and $MT_2$ receptors, and the antagonism of serotonergic $5\text{-HT}_{2C}$ receptors. Although its use is approved for the treatment of depression, some studies indicate potential to be used in the treatment of generalized anxiety disorder (Levitan, N M et al. *em Exp. Clin. Psychopharmacol.* 2012, 20(6): 504-509 —*A review of preliminary observations on agomelatine in the treatment of anxiety disorders*).

Although there are several options for treating anxiety disorders, all drugs developed so far present negative features, many of which interfere with its clinical use. Among them, there should be highlighted the trend of benzodiazepines in developing physical dependence, issues related to withdrawal syndrome observed in all classes of medicines mentioned and, when considering the two classes of medicines more employed nowadays for the treatment of anxiety disorders, ISRS and IRSN, besides of the withdrawal syndrome triggered by an abrupt interruption of medication, the use of these inhibitors is associated with a high percentage in triggering some kind of sexual dysfunction, which negatively interferes on patient compliance to treatment.

Among the current possibilities for treating anxiety disorders, the need in developing medicines with greater efficiency and less prone to induce withdrawal syndrome still exists.

Surprisingly, it was found that the compounds of general formula (I), where R1 is —$OCH_3$ or —CN, are potent anxiolytic.

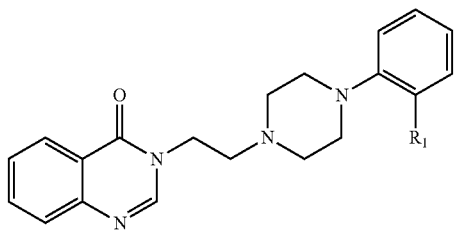

A complementary study conducted with the compound of general formula (I), where R1 is —OCH$_3$, showed that, besides of being anxiolytic, this compound cannot trigger the withdrawal syndrome.

DESCRIPTION OF THE INVENTION

Figure 1:
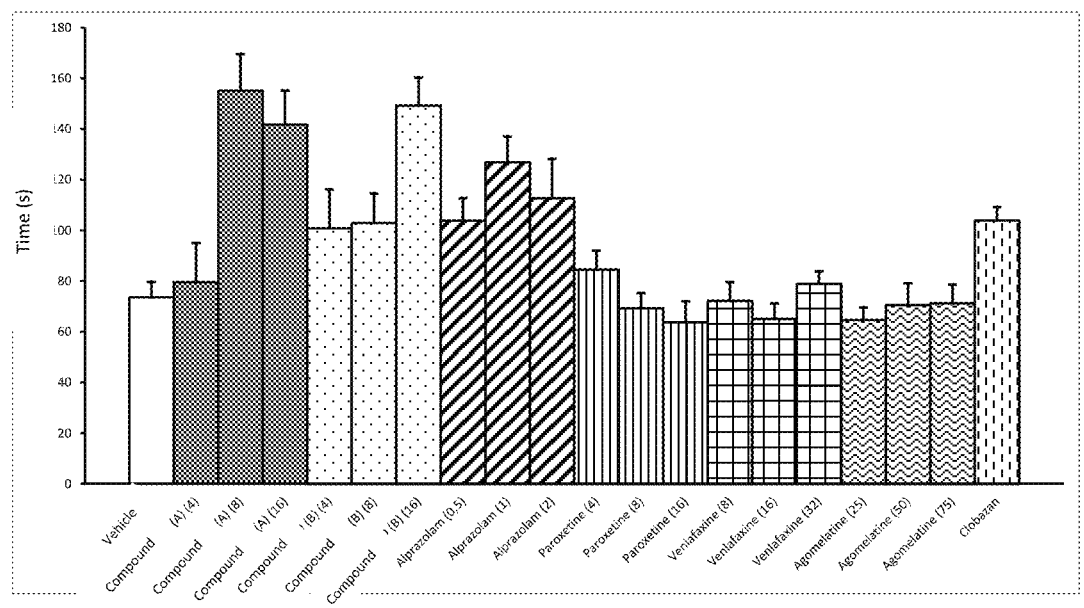
FIG. 1: Average time of permanence in the clear compartment, in seconds, on the bright/dark box test to the compounds tested.

The present invention is a method for treating comorbid anxiety disorders and depression disorders, as well as for preventing depression disorders in individuals affected by anxiety disorders, by administering a therapeutically effective amount of the compound of general formula (I):

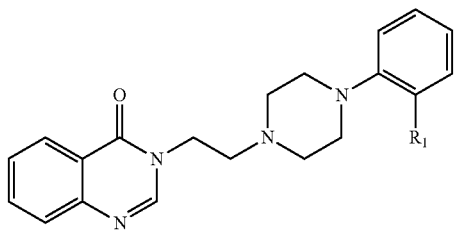

wherein
R$_1$ is (—OCH$_3$) or (—CN),
its suitable pharmaceutical salts, hydrates or anhydrates thereof.

The anxiety disorders may include panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to general medical condition, substance-induced anxiety disorder and anxiety disorder without specific cause.

Depression disorders may include major depression disorder, dysthymia disorder, non-specific depression disorder, psychotic depression, postpartum depression, seasonal affective disorder and bipolar disorder.

Comorbidity between anxiety and depression disorders tends to considerably worsen mental condition in patients affected by these disorders. In these cases, it is common to observe that the treatment provided by conventional antidepressants is considerably less effective than the response triggered in merely depressed patients.

The compound of general formula (I), its suitable pharmaceutical salts, hydrates and anhydrates may be administered pure or as a pharmaceutical composition. Thus, the present invention is also directed to a pharmaceutical composition for treating comorbid anxiety disorders or not depression disorders, which comprises a therapeutically effective amount of the compound of general formula (I), or a suitable pharmaceutical salt, their hydrates or anhydrates, associated with at least one suitable pharmaceutical excipient.

Studies previously cited have shown a high incidence of patients with depression disorders co-occurring with anxiety disorders. These studies also showed that a significant portion of patients with this comorbidity initially presented some kind of pure anxiety disorder. This seems to indicate a tendency of people with anxiety disorders in developing, lately, any depression disorder.

Thus, this invention also aims at using the compound of general formula (I), its suitable pharmaceutical salts, its hydrates and anhydrates in the preventive treatment of depression disorders selected from the group consisting of: major depressive disorder, minor dysthymic depression disorder and atypical disorders such as psychotic depression, postpartum depression, seasonal affective disorder and bipolar disorder, which consists of administering a therapeutically effective amount of this compound in patients with anxiety disorders selected from the group consisting of: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to general medical conditions, substance-induced anxiety disorder and anxiety disorder without specific cause.

In the present invention, the compound of general formula (I) is basic in nature and can form addition salts with many organic and inorganic acids. Examples of organic acids adequate to the preparation of their addition organic salts are fumaric, acetic, propionic, benzoic, ascorbic, pamoic, succinic, oxalic, tartaric, citric, lactic, malic, stearic, palmitic, benzenesulfonic, p-toluenesulfonic, methanesulfonic, ethanesulfonic, aspartic, mandelic, cinnamic, glycolic, gluconic, glutamic and p-amino-benzoic acid, among others. Examples of inorganic acids are hydrochloric, hydrobromic, sulfuric, phosphoric and nitric, among others.

The preparation of acid addition salts of the compound of general formula (I) can be accomplished using common techniques described in the state of the art, for example, through the treatment of the compound in its base form with a molar amount equivalent to or in excess of the selected acid, using organic solvents, mixtures of organic solvents and mixtures between organic solvents and water.

The compound of general formula (I), its suitable pharmaceutical salts, hydrates and/or anhydrates may be administered pure or as a pharmaceutical composition. When administered as a pharmaceutical composition, it will be associated with at least one conventional or adequate pharmaceutical excipient.

According to the present invention, the compound of general formula (I) comprises the methoxy-substituted derivative (wherein R$_1$=—OCH$_3$), whose chemical name is 3-(2-(-4-(2- methoxyphenyl)piperazin-1-yl)ethyl)quinazolin-4(3H)-one (compound A), and the cyano-substituted derivative, whose chemical name is 3-(2-(4-(2-cyanophenyl)piperazin-1-yl) ethyl)quinazolin-4(3H)-one (compound B). Their structures are represented below:

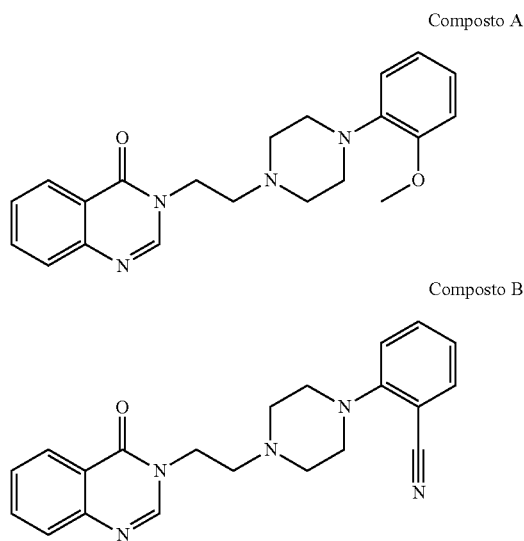

Composto A

Composto B

According to the present invention, a conventional or appropriate pharmaceutical excipient is any substance other than the active pharmaceutical ingredient which has been evaluated properly as to its safety and that has been intentionally included in a pharmaceutical dosage form.

The choice of excipients to be used in the preparation of pharmaceutical compositions is usually performed taking into consideration the route of administration, the physical-chemical compatibility of the excipient with the active ingredient, the form of preparation of the pharmaceutical form and its effect on efficacy. Such excipients are well known in the art and are described in the literature widely used by people skilled in the art (for example, *Handbook of Pharmaceutical Manufacturing Formulations*—Vol. 1 a 6—2004—Sarfaraz K. Niazi—CRC Press and Remington's Pharmaceutical Sciences, Mack Publishing).

Pharmaceutical excipients are usually classified or sub-classified according to their function in pharmaceutical compositions and/or in their manufacturing technique. They can be diluents, binders, disintegrants or disagregants, lubricants, suspending agents, thickeners, agents, solvents, surfactants, glidants, anticaking agents or flow agents, coating agents, plasticizers, sweeteners, isotonicity agents, dyes, preservatives, antioxidants, pH modifier or control agents, complexing agents used to mask taste, improve solubility, promote stability of the formulation, and modulate bioavailability, chelating agents, fragrances and flavoring agents.

Diluents are pharmaceutical excipients incorporated into solid dosage forms such as tablets, capsules, dragees, pellets, powders and granules in order to increase the volume or weight of the dosage form. They can also be used in liquid and semi-solid pharmaceutical forms with the same purpose. Examples of suitable diluents adequate to prepare the pharmaceutical composition of this invention include, without limitation: calcium carbonate, calcium phosphates, calcium sulphate, microcrystalline cellulose, powdered cellulose, dextrins, dextrose, fructose, kaolin, anhydrous and/or mono-hydrate lactose, maltose, sorbitol, starches (of maize, wheat, potato, tapioca), pregelatinized starch, sucrose and sugar.

Binders are pharmaceutical excipients that are incorporated into formulations in order to facilitate agglomeration of powders, forming granules during the mixing step (or granulation), employing water as granulation fluid, water-alcohol mixtures or other solvents. Binders can also be employed in dry mix process, without the need for fluids. Examples of suitable binders for the preparation of pharmaceutical compositions of the present invention includes, without limitation: acacia, alginic acid, ammonium methacrylate copolymer, carbomer copolymer, homopolymer or interpolymer, starches (maize, wheat, potato, tapioca), microcrystalline cellulose, methylcellulose, ethylcellulose, hydroxypropylmethylcellulose, dextrin, maltodextrin, maltose, sucrose, gelatin, glucose, guar gum and povidone.

Disintegrants or disagregants are pharmaceutical excipients capable of accelerating disintegration or dissolution of the formulation when in contact with biological fluids. Examples of disintegrants or disagregants suitable to prepare the pharmaceutical composition of this invention include, without limitation: alginic acid, starches, sodium alginate, sodium croscaramelose, sodium glycolate, sodium carboxymethyl cellulose, microcrystalline cellulose and crospovidone.

Lubricants are excipients that promote friction reduction between the particles present in the formulations and also reduce friction between particles and the walls of the equipment employed in their preparation. Examples of lubricants suitable to the preparation of the pharmaceutical composition of the present invention include, without limitation: calcium stearate, magnesium stearate, zinc stearate, mineral oil, polyethylene glycol, sodium lauryl sulfate, sodium stearyl fumarate, starch, stearic acid, talc and hydrogenated vegetable oil type I.

Suspending agents and thickeners are excipients used in formulations to promote stability of dispersed systems (for example, suspensions and emulsions), to reduce the sedimentation rate of particles or to reduce fluidity of liquid formulations. Examples of suspending agents and thickeners appropriate to the preparation of the pharmaceutical composition of the present invention include, without limitation: acacia, agar, alginic acid, aluminum monostearate, bentonite, carbomer, carbomer copolymer, carbomer homopolymer, carbomer inerpolymer, sodium or calcium carboxymethyl cellulose, carrageenan, microcrystalline cellulose, guar gum, gelan gum, hydroxyethylcellulose, hydroxypropyl cellulose, methylcellulose, magnesium aluminum silicate, pectin, polyethylene oxide, polyvinyl alcohol, povidone, propylene glycol alginate, sodium alginate, silicon dioxide, colloidal silicon dioxide, starches (corn, wheat, potato, tapioca), tragacanth gum and xanthan gum.

Solvents are excipients used to dissolve other substances in the preparation of liquid, semi-solid and solid compositions, the latter being employed to facilitate mixing and/or provide a mixing means with homogeneous concentration of active pharmaceutical ingredient or other excipient. Examples of solvents suitable to the preparation of pharmaceutical composition of the present invention include, without limitation: water, ethanol, isopropanol, vegetable oils (corn, cotton, sesame, soy), mineral oil, glycerin, sorbitol and oleic acid.

Surfactants, also known as surface tension, modulators of surface tension, are excipients that have various functions, serving as emulsifiers, wetting and/or solubilizing agents. Examples of appropriate surfactants to be used in the preparation of the pharmaceutical composition of the present invention include, without limitation: benzalkonium chloride, benzethonium chloride, cetylpyridinium chloride, nonoxinol 9, octoxynol 9, polyoxyl stearate 50, polyoxyl oleic ether 10, polyoxyl cetostearyl ether 20, polyethoxylated castor oil 35, hydrogenated polyethoxylated castor oil 40, polyoxyl stearate 40, polyoxyl lauryl ether, polyoxyl stearyl ether, polysorbate 20, polysorbate 40, polysorbate 60, polysorbate 80, sodium ketostearyl sulphate, sodium lauryl sulfate, sorbitan monolaurate, sorbitan sesquioleate, sorbitan monopalmitate, sorbitan sesquioleate, sorbitan trioleate, cetyl alcohol, oleic alcohol, propylene glycol monostearate poloxamer, carbomer copolymer or interpolymer, cholesterol, monoethanolamine, diethanolamine, triethanolamine, diethylene glycol stearates, sodium docusate, ethylene glycol stearates, glyceryl distearates, glyceryl monolinoleate, glyceryl monooleate, glyceryl monostearate, lanolin alcohols, lecithin, mono and diglycerides, sodium stearate, stearic acid and emulsifying wax.

Flow agents, anticaking agents or glidants are excipients used in formulations to promote flow and reduce formation of clusters in solid conductor tapers during processing and flowing of powders. Examples of flow agents, anticaking agents or glidants suitable for the preparation of the pharmaceutical composition of the present invention include, without limitation: calcium silicate, magnesium silicate, colloidal silicon dioxide and talc.

The coating agents are excipients used for several functions, among them, masking unpleasant flavors or odors, controlling drug release rate, improving appearance, ease of swallowing and for controlling drug release in the gastrointestinal tract (e.g., enteric coating). Examples of coating agents suitable for preparing the pharmaceutical composition of this invention includes, without limitation: ammonium methacrylate copolymer, sodium carboxymethyl cellulose, cellulose acetate phthalate, cellulose acetate, copovidone, ethylcellulose and aqueous dispersions thereof, gelatin, pharmaceutical glazes, hydroxypropyl cellulose, hydroxypropylmethyl cellulose, cellulose acetate succinate hydroxypropylmethyl, hydroxypropylmethyl cellulose phthalate, maltodextrin, methacrylic acid copolymer and its dispersions, methylcellulose, polyethylene glycol, polyvinyl acetate phthalate, shellac, pregelatinized modified starch, sucrose, titanium dioxide, carnauba wax and microcrystalline wax.

Plasticizers are excipients added to other substances in order to give plasticity and resilience (elasticity). They are important components to provide the appropriate physical properties of polymeric systems. Examples of plasticizers adequate to be used in the preparation of the pharmaceutical composition of this invention include, without limitation: acetyl tributyl citrate, acetyl triethyl citrate, castor oil, diacetylated monoglycerides, dibutyl sebacate, sorbitol, dextrin, diethyl phthalate, glycerin, polyethylene glycol, monomethyl polyethylene glycol ether, propylene glycol, benzyl benzoate, triacetin, tributyl citrate, triethyl citrate and chlorobutanol.

Isotonic solutions are commonly employed for parenteral administration, i.e., solutions with osmotic pressure similar to the tissues with which they come into contact in order to avoid hemolysis, reduce pain and discomfort during administration. Examples of isotonic agents usually employed to provide isotonicity to the pharmaceutical composition of this invention include, without limitation: dextrose, glycerine, mannitol, sodium chloride and potassium chloride.

Sweeteners are agents used to mask unpleasant flavors and sweeten oral formulations. Examples of appropriate sweeteners in the preparation of the pharmaceutical composition of the present invention include, without limitation: acesulfame potassium, aspartame, aspartame-acesulfame salt, dextrates, dextrose, fructose, galactose, maltose, maltitol, mannitol, saccharin, calcium saccharin, sodium saccharin, sorbitol, sucralose, sucrose, sugar and tagatose.

Pharmaceutical dyes are also part of the scope of compositions of this invention, which are incorporated into dosage forms in order to provide a distinct appearance to each medicine, facilitating the differentiation of a specific formulation among formulations with similar physical aspects. Examples of adequate pharmaceutical dyes to be used in the composition of the present invention include: red ferric oxide, yellow ferric oxide, ferric oxide blends, caramel, titanium dioxide, FD&C dyes and D&C dyes.

Depending on the route of administration and the physical-chemical properties inherent to the compounds of this invention, substances able to stabilize, preserve, prevent and/or avoid premature degradation of its constituents may be added to the pharmaceutical composition prepared with these compounds. These additional excipients may act as antioxidants, preservatives and pH modifiers or regulators. Examples of used excipients having these properties that are suitable for the preparation of the pharmaceutical composition of the present invention include, without limitation: ascorbic acid, sorbic acid, sodium metabisulfite, alpha-tocopherol, methyl paraben, propyl paraben, butylparaben, sodium sulfite, butylated hydroxytoluene (BHT), butylated hydroxyanisole (BHA), phenol, benzyl alcohol, benzalkonium chloride, benzethonium chloride, cetylpyridinium chloride, benzoic acid, sodium benzoate, sodium propionate, boric acid, and pH control agents, the latter comprising the organic and inorganic acids, bases and buffers usually employed in pharmaceutical compositions.

The pharmaceutical composition comprising the compound of general formula (I), its suitable pharmaceutical salts, hydrates and/or anhydrates thereof may additionally contain substances or preparations: (a) complexing agents to mask flavor, improve solubility, promote stability of the formulation and/or modulate bioavailability, and (b) fragrances and flavoring agents used to neutralize or mask unpleasant odors and flavors, or to give pleasant odors and flavors. Many substances and preparations are available in the market for such applications, and its use is limited to approved or duly certified agents, which are compatible with the ingredients of the composition.

For delivery and therapeutic administration, the compound of general formula (I), its pharmaceutically acceptable salts, hydrates and/or anhydrates thereof, a formulation in the form of compositions suitable for oral, parenteral, nasal, rectal, transdermal and transmucosal administration employing conventional techniques and suitable excipients may be prepared. Thus, this compound can be prepared in the form of tablets, pills, capsules, dragees, granules, powders, pellets, aerosols, elixirs, solutions, lyophilized material, suspensions, syrups, suppositories and patches, among other known forms adequate to routes of administration.

The therapeutic dose to be employed in the compound of general formula (I) must be planned and calculated according to the chosen route of administration, the weight and condition of the patient and the severity of the disorder to be treated. Generally, this compound is administered in therapeutically effective doses ranging from about 0.1 mg to about 1,000 mg/day, preferably from 0.5 mg to 500 mg/day, still more preferably from 1 mg to 250 mg/day, administered as a single or split dose.

Examples

Examples of the compound of general formula (I), Compound A and Compound B, undergone specific animal models of anxiety, such as, the bright/dark box model test and the sphere hiding test. Additionally, compound A was subjected to non-precipitated abstinence test, by which it was demonstrated that it does not trigger the withdrawal syndrome, a unique and non-observed advantage in medicines used for the treatment of anxiety disorders.

Bright/Dark Box Test

This model, also known as clear/dark transition test, is characterized as a model of conflict, based on the natural tendency to explore new environments versus avoidance of doing so, due to the potential possibility of the presence of aversive stimuli. It is an animal model based on independent behavior of conditioning, therefore, there is no need of learning. In rodents, this model is grounded in their natural aversion to excessively clear environments. This aversion is measured from the ansiogenic component expressed by lower exposure of the animal to the clear compartment.

Description of the Method:

The method employed followed the procedure described by Crawley and Goodwin (*Pharmacol. Biochem. Behav.* 1981, 15, 695-699).

The animals were placed on the clear field of a box comprising two compartments, one being illuminate and open (25×27×27 cm) and the other being dark and close (20×27×27 cm). Data on the length of stay in each compartment were collected over the three-minute test.

This test aimed at obtaining a comparison profile of response of Compound (A) (3-(2-(-4-(2-methoxyphenyl)piperazin-1-yl)ethyl)quinazolin-4(3H)-one and Compound (B) 3-(2-(4-(2-cyanophenyl)piperazin-1-yl)ethyl)quinazolin-4(3H)-one with known compounds that act by different mechanisms. The comparative compounds were alprazolam (benzodiazepine), paroxetine (ISRS-type antidepressant), venlafaxine (IRSN-type antidepressant) and agomelatine (antidepressant that acts on melatonin and serotonin 5-HT$_{2C}$ receptor). The following doses were employed in this study:

TABLE 1

Tested compounds, concentrations and route of administration.

| Compound | Concentration | Route of administration |
|---|---|---|
| Compound (A) | 4, 8 and 16 mg/Kg | Intraperitoneal (i.p.) |
| Compound (B) | 4, 8 and 16 mg/Kg | Intraperitoneal (i.p.) |
| Alprazolam | 0.5, 1.0 and 2 mg/Kg | Intraperitoneal (i.p.) |
| Paroxetine | 4, 8 and 16 mg/Kg | Intraperitoneal (i.p.) |
| Venlafaxine | 8, 16 and 32 mg/Kg | Intraperitoneal (i.p.) |
| Agomelatine | 25, 50, and 75 mg/Kg | Intraperitoneal (i.p.) |

In this blind study, ten mice (RJ:NMRI, males) were employed per group. Clobazam (12 mg/Kg, i.p. route) was administered under the same study conditions as the reference compound. All compounds were administered 30 minutes before the test.

The test data of the response of substances were analyzed comparing the groups treated with the control vehicle using one-way ANOVA followed by post-hoc analysis of Dunnett's test. The data of the reference substance obtained were analyzed using unpaired Student's t test.

Results

Data regarding time spent by mice in the clear compartment are presented in table 2:

TABLE 2

Time spent in the clear compartment

| Treatment | Time spent in the clear compartment (seconds) (mean ± mean standard error) | compared to vehicle (1) | (2) | % |
|---|---|---|---|---|
| Vehicle | 73.6 ± 6.1 | | | |
| Compound (A)-(4) | 79.6 ± 15.4 | | NS | +8% |
| Compound (A)-(8) | 155.1 ± 14.4 | | *** | +111% |
| Compound (A)-(16) | 141.7 ± 13.4 | | *** | +93% |
| Compound (B)-(4) | 100.9 ± 15.2 | | NS | +37% |
| Compound (B)-(8) | 103.0 ± 11.5 | | NS | +40% |
| Compound (B)-(16) | 149.3 ± 11.0 | | *** | +103% |
| Alprazolam (0.5) | 103.9 ± 11.5 | | NS | +41% |
| Alprazolam (1) | 126.9 ± 10.1 | | *** | +72% |
| Alprazolam (2) | 112.7 ± 15.5 | *** | NS | +53% |
| Paroxetine (4) | 84.6 ± 7.4 | | ** | +15% |
| Paroxetine (8) | 69.3 ± 5.9 | | NS | −6% |
| Paroxetine (16) | 63.8 ± 8.2 | | NS | −13% |
| Venlafaxine (8) | 72.3 ± 7.3 | | NS | −2% |
| Venlafaxine (16) | 65.1 ± 6.0 | | NS | −12% |
| Venlafaxine (32) | 78.9 ± 4.9 | | NS | +7% |
| Agomelatine (25) | 64.7 ± 4.9 | | NS | −12% |
| Agomelatine (50) | 70.6 ± 8.5 | | NS | −4% |
| Agomelatine (75) | 71.3 ± 7.3 | | NS | −3% |
| Clobazam (12) | 104.0 ± 5.2 | ** | | +41% |

Comparison between groups:
NS = not significant;
* = $p < 0.05$;
** = $p < 0.01$;
*** = $p < 0.001$ (3): For testing and comparison of groups treated with substances: one-way ANOVA with the group as a factor. For the reference treated group: unpaired Student's t Test (4): Dunnett test when the one-way ANOVA value was significant Results The results presented in table 2, whose graph can be observed in FIG. 1, demonstrate that the Compounds (A) and (B) were efficient in extending the permanence time in the clear compartment of the experimental model. For Compound (A), the permanence time in the clear portion of the model was significant for concentrations 8 mg/Kg and 16 mg/Kg, while for Compound (B), this modification was significant for concentration 16 mg/Kg. Alprazolam presented significant activity at 1 mg/kg, and did not achieve significant activity in the other concentrations tested. Although the results were not statistically significant in other concentrations tested both for alprazolam as for compound (B), they were in the limit, and it can be observed that the results achieved indicate a trend of increase of permanence time in the clear compartment of the model.

Sphere Hiding Test

This test is based on the natural aversive behavior to glass and marble of rodents, where the presence of these objects triggers the action of burying (hiding). In this test, there are potential behavioral changes of medicines that may promote an ansiogenic or anxiolytic profile. This is determined by the increase or decrease of the behavior of hiding glass spheres ("marbles") that are randomly distributed on the surface of a box lined with sawdust. The increase of the number of covered balls is an indicative of anxiety, since it is supposed to represent a foreign agent to the animal, whose presence may pose threat. The administration of anxiolytics medicines decreases the number of spheres buried in non-sedative doses.

Description of the Method

The method employed followed the procedure described by Broekkamp et al. (*Eur. J. Pharmacol.*, 1986, 126, 223-229).

Mice were individually placed in transparent plastic cages (33×21×18 cm), with the floor covered by a 5 cm layer of sawdust and 25 glass spheres grouped in the center of the cage. The cage was covered with a perforated plastic cover. Each test cage, along with the glass spheres, were previously impregnated with "mouse odor", and a group of 10 mice was left inside for 15 minutes.

The number of glass spheres covered with sawdust (⅔ or more of the surface) was counted at the end of the 30 minutes of the test.

Each study group consisted of 12 mice. The test was partially blind (substances tested versus vehicle of the tested substances).

This test aimed at obtaining a comparison profile of response of Compound (A) (3-(2-(-4-(2-methoxyphenyl)piperazin-1-yl)ethyl)quinazolin-4(3H)-one and Compound (B) (3-(2-(4-(2-cyanophenyl)piperazin-1-yl)ethyl)quinazolin-4(3H)-one) with known compounds that act by different mechanisms. The comparative compounds used were alprazolam (benzodiazepine) and paroxetine (ISRS-type antidepressant). These compounds were tested in the following doses:

TABLE 3

Compounds tested, concentrations employed and route of administration.

| Compound | Concentration | Route of administration |
| --- | --- | --- |
| Compound (A) | 8, 16 and 32 mg/kg | Intraperitoneal (i.p.) |
| Compound (B) | 8, 16 and 32 mg/kg | Intraperitoneal (i.p.) |
| Alprazolam | 1.0 mg/kg | Intraperitoneal (i.p.) |
| Paroxetine | 1.0 mg/kg | Intraperitoneal (i.p.) |

Fluoxetine (ISRI antidepressant) was used as the positive control substance in the test, and was administered at 32 mg/kg (i.p.).

Quantitative data for the tested substances (number of glass spheres coated with sawdust) were evaluated by comparison with the treated groups using one-way ANOVA followed by planned comparisons against the appropriate vehicles. Data with fluoxetine were compared to the vehicle control using unpaired Student's t test.

Results

The results related to the number of hidden spheres for each group treated are presented in table 4:

TABLE 4 hidden spheres in each group treated

| | Number of Hidden Spheres | | | |
| --- | --- | --- | --- | --- |
| Treatment | (mean ± mean standard error) | Compared to vehicle control | | |
| | | (1) | (2) | % |
| Vehicle | 19.1 ± 2.0 | | | |
| Compound (A)-(4) | 3.5 ± 2.4 | | ** | −82% |
| Compound (A)-(8) | 0.3 ± 0.3 | | ** | −98% |
| Compound (A)-(16) | 0.1 ± 0.1 | | ** | −99% |
| Compound (B)-(4) | 11.0 ± 3.3 | | * | −42% |
| Compound (B)-(8) | 2.1 ± 2.1 | | ** | −89% |
| Compound (A)-(16) | 0.0 ± 0.0 | | ** | −100% |
| Alprazolam (1) | 1.6 ± 1.4 | | ** | −92% |
| Paroxetine (1) | 8.4 ± 2.3 | | ** | −56% |
| Fluoxetine (32) | 4.9 ± 2.0 | *** | | −74% |

Figure 2:
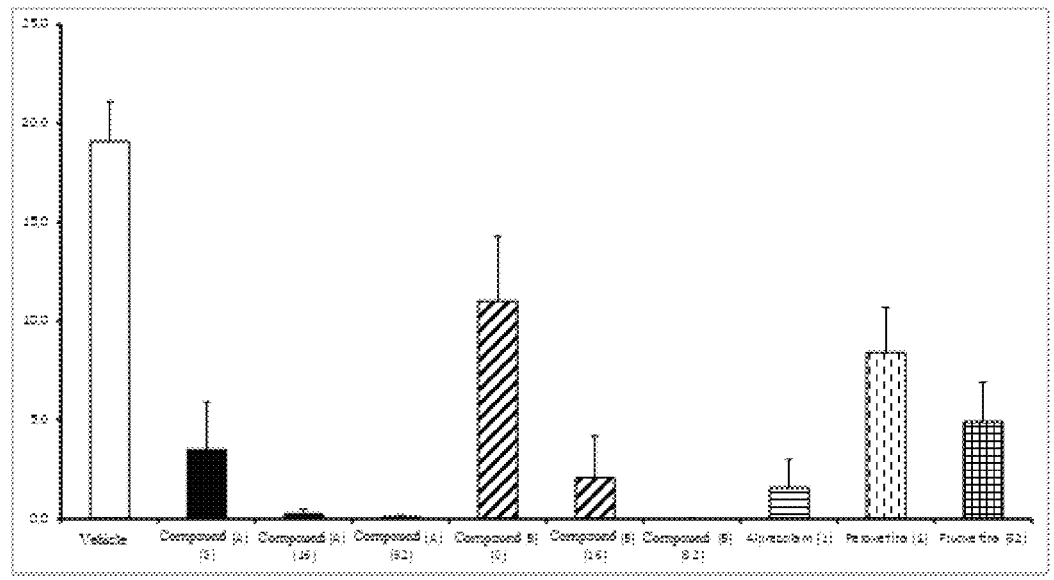
FIG. 2: Average number of spheres covered with sawdust on the test of hiding spheres to the compounds tested.

Comparison between groups:
NS = not significant;
* = $p < 0.05$;
** = $p < 0.01$;
*** = $p < 0.001$ (3): For testing and comparison of groups treated with substances: one-way ANOVA with the group as a factor. For the reference treated group: unpaired Student's t Test (4): Dunnett test when the one-way ANOVA value was significant The results presented in table 4, whose graph is shown in FIG. 2, show that all substances tested were effective in reducing the number of hidden spheres. Compounds (A) and (B) significantly reduced the number of hidden spheres and this behavior has been shown to be dose-dependent.

Non-Precipitated Withdrawal Test

This test aims at assessing how the sudden cessation of the administration of a medicine can be associated with the occurrence of withdrawal identifiable symptoms. The types of symptoms examined are feed changes, weight gain, body temperature and the occurrence of one or behavioral symptoms and others, such as tremor, teeth chattering, wet dog body-shaking, diarrhea or piloerection. The triggering of these signs is a first sign that the substance induces dependence after repeated administration.

Description of the Method

The method employed followed the procedure described by Goudie and Leathley (Psychopharmacology 1991, 103: 529-537).

Two mice per cage received two administrations per day (approximately 10:00 hours and 16:00 hours) of the test substance continuously during 19 days (day 1 to day 19), with the last administration occurring next to 10:00 hours of the 20$^{th}$ day. Control animals received the same number of administrations of vehicle. After discontinuation of the medicine, rats were not observed for a period of 8 days with regard to changes in food consumption, body weight and rectal temperature. Additionally, they were observed with regard to behavioral manifestations, including the following items: jump, reactions to sound stimuli (snap of the fingers), sniffing, wet dog body-shaking, stretching, ptosis, tremor, genital discharge, scratching behavior, hyperactivity, grooming, straub tail, walk on tip of paws, teeth chattering, dyspnea, diarrhea and burying behavior. During the discontinuation phase, all animals received administration of vehicle once a day.

Additionally to the observations made after discontinuing the medicines, the same measures were taken at day 1 and day 10 of treatment, in addition to the 3 last days (days 18 to 20) immediately prior to administration of the dose in the morning to assess the effects of medicines before discontinuation. After discontinuation, the first observation was performed 24 hours after the last administration and, from then on, every 24 hours (days 21 to 28).

For daily measurements, the animals were evaluated with respect to behavioral changes during 5 minutes (two animals simultaneously observed). Then, their body weights and rectal temperatures were measured. Then, they received the proper treatment and were returned to their cages.

The leftover food in their supporters was weighed immediately after all animals return to their cages (only in the mornings), and food consumption in the previous 24 hours was determined.

The body weights, feed consumption and rectal temperatures were also measured 24 hours before the first administration, as reference values. The treated groups were homogenized with regard to body weights on the day preceding the first administration of the tested substances.

Compound (A) (3-(2-(-4-(2-methoxyphenyl)piperazin-1-yl)ethyl)quinazolin-4(3H)-one) was evaluated in 3 doses (3, 10 and 30 mg/kg) administered orally (p.o.) and compared to the vehicle (control group).

Chlordiazepoxide (64 mg/kg, p.o.) was administered under the same experimental conditions, and was employed as reference substance in the test.

Paroxetine (15 and 30 mg/kg p.o.) was administered under the same experimental conditions and was used as comparative substance.

The test was blinded. Data were analyzed by comparing substances with their control vehicles employing one-way ANOVA with the group as a factor followed by post-hoc Dunnett tests. Data with the reference substance were analyzed using unpaired Student's t test.

Results

Figure 3:
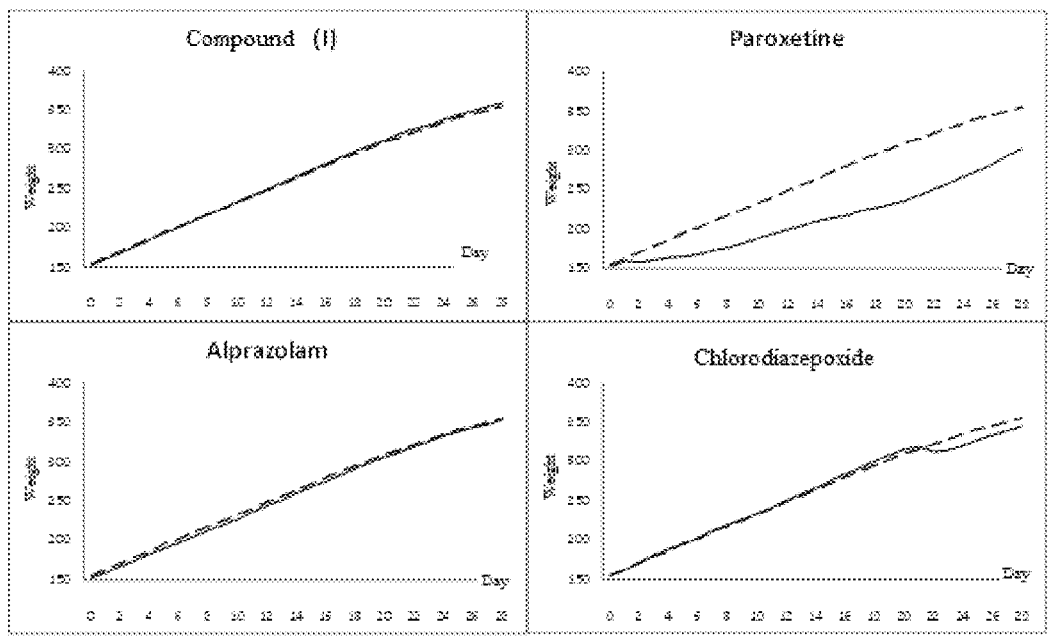
FIG. 3: Body weight variation test in the test of not precipitated abstinence over the days to the compounds tested.
Figure 4:
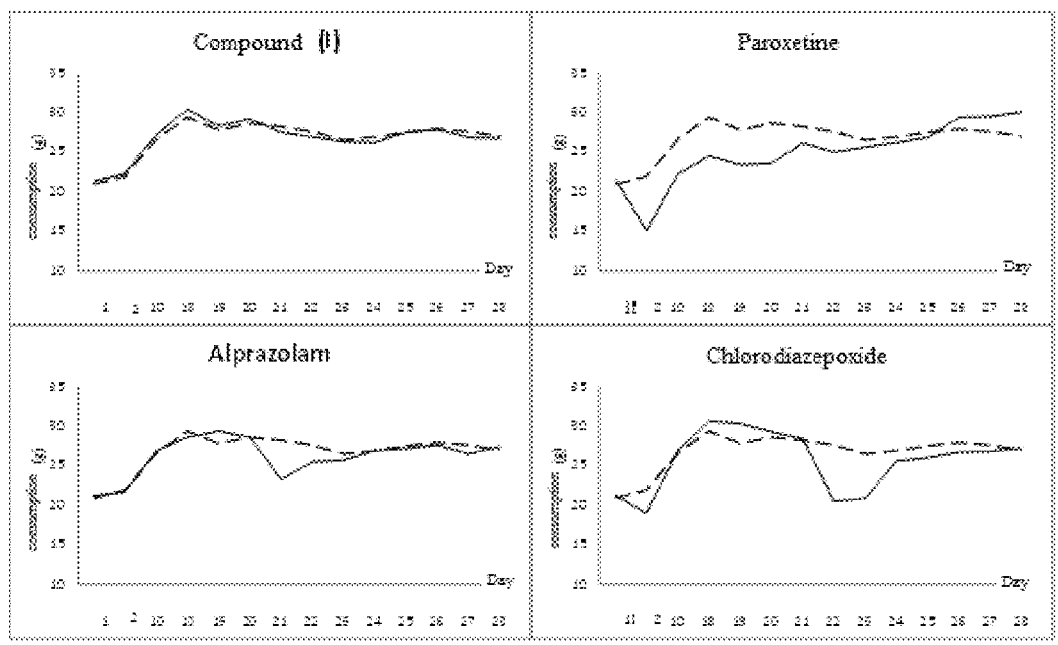
FIG. 4: Variation of food consumption in the test of non-programmed abstinence over the days to the compounds tested.
Figure 5:
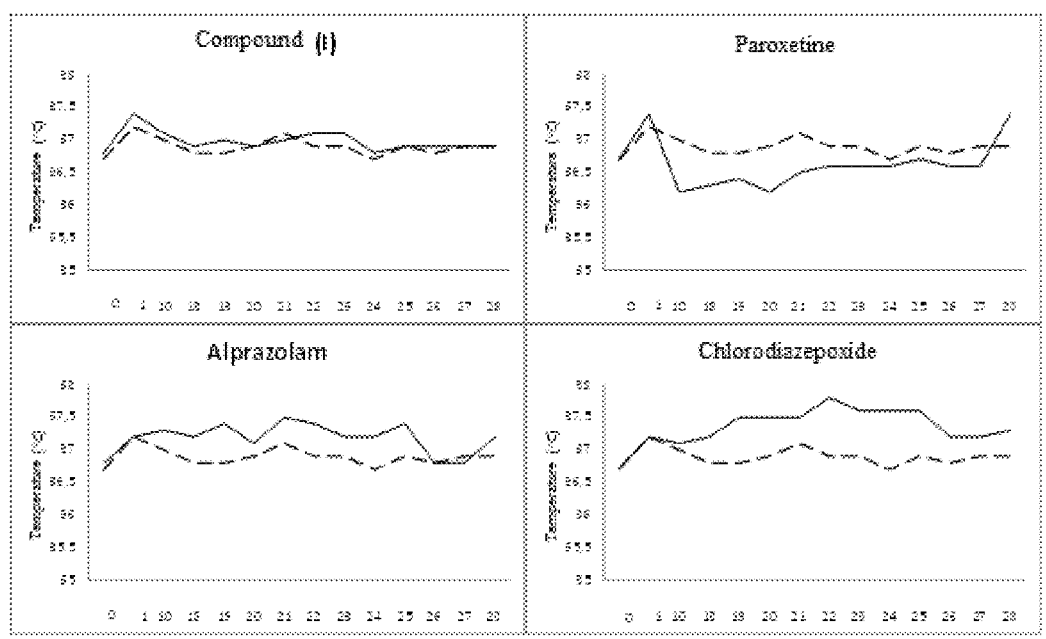
FIG. 5: Variation of rectal temperature in the test of non-programmed abstinence over the days to the compounds tested.

The results observed in this experiment with respect to body weight, daily quantity of food consumption and rectal temperature are presented in the graphs of FIGS. 3 to 5, which present data of the substances tested in their higher doses. In these graphs, the dotted line curve corresponds to the response obtained for the vehicle, while full line curve corresponds to the response obtained for each test substance.

It can be observed from the graphs shown in FIGS. 3 to 5 that Compound (A) does not trigger statistically significant alterations compared to the standard (vehicle) in terms of body weight, amount of food consumed and rectal temperature parameters. Paroxetine significantly induced weight loss and reduction of food consumption during the treatment period. During the withdrawal period, there was a significant increase in the amount of food consumed, which was higher than the one observed in the group treated with vehicle. Alprazolam, during treatment, showed no significant changes regarding the three studied parameters. During the withdrawal period, it induced a significant reduction in the amount of food consumed on the first day of abstinence. Chlordiazepoxide did not induce significant changes in body weight and amount of food consumed parameters in the treatment phase. There was also a slight increase of rectal temperature at this phase. At the withdrawal phase, there was a clear reduction in body weight and the amount of food consumed, and a significant increase of rectal temperature.

The following behavioral effects and psychological symptoms were observed for the vehicle and tested substances:

f) Vehicle: Behavioral or psychological effects were not observed during the treatment or in the withdrawal period.
g) Compound (A): Behavioral or psychological effects were not observed during the treatment or in the withdrawal period at any dose used in the experiment.
h) Paroxetine: Behavioral or psychological effects were not at a dose of 15 mg/kg. At 30 mg/kg, it induced behavioral and psychological effects (ptosis and teeth chattering) in the treatment phase. In the withdrawal period, it induced occasional burying behavior, dyspnoea, piloerection, ptosis, scratching behavior, wet dog body-shaking and contortions.
i) Alprazolam: During the treatment phase at both concentrations tested, it induced hyperactivity, jumps and dyspnoea. In the withdrawal phase, it triggered occasional diarrhea in a rat.
j) Chlordiazepoxide: During the treatment phase, it induced behavioral and psychological effects as ptosis, hyperactivity, jumps and dyspnoea. In the withdrawal phase, it intensified the psychological behaviors and symptoms, mainly dyspnoea and hyperactivity, inducing occasional straub tail and teeth chattering.

The observations performed in this experiment suggest that compound (A) does not induce withdrawal syndrome after an extended administration regimen. Paroxetine induces mild withdrawal syndrome. Alprazolam induces withdrawal syndrome which can be evidenced by reduction of the amount of food consumed. Chlordiazepoxide induces a clear withdrawal syndrome, with body weight reduction, reduction of the amount of food consumed and increase of rectal temperature.

The results obtained in the models of anxiety (clear-dark box and sphere hiding tests) demonstrate that Compounds (A) and (B) (3-(2-(-4-(2-methoxyphenyl)piperazin-1-yl)ethyl)quinazolin-4(3H)-one and 3-(2-(-4-(2-cyan)piperazin-1-yl)ethyl)quinazolin-4(3H)-one, respectively) have an extremely promising activity profile, both exhibiting anti-anxiety properties higher than compounds tested in parallel.

Moreover, the non-precipitated withdrawal test with Compound (A) showed that this compound does not induce withdrawal syndrome, a very promising result, and may prove to be typical for this family of compounds.

The invention claimed is:

1. A method for treating comorbid anxiety disorder and depression disorders in a subject in need thereof, comprising administering a therapeutically effective amount of the compound of general formula (I):

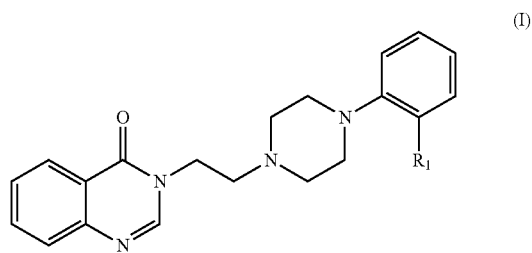

(I)

wherein $R_1$ is —$OCH_3$ or —CN,
or suitable pharmaceutical salts, hydrates or anhydrates thereof.

2. The method of treatment, according to claim 1, wherein the anxiety disorder is one or more selected from the group consisting of panic disorder with or without agoraphobia, agoraphobia without history of panic disorder, specific phobia, social phobia, obsessive-compulsive disorder, post-traumatic stress disorder, acute stress disorder, generalized anxiety disorder, substance-induced anxiety disorder and anxiety disorder without specific cause.

3. The method of treatment, according to claim 1, wherein the depression disorder is one or more selected from the group consisting of major depression disorder, dysthymia disorder, non-specific depression disorder, psychotic depression, post-partum depression, seasonal affective disorder and bipolar disorder.

4. The method of treatment, according to claim 1, wherein the therapeutically effective amount of the compound of general formula (I) is from about 0.1 mg/day to about 1,000 mg/day, administered as single dose or in fractions.

\* \* \* \* \*